US012625555B1

(12) United States Patent
Vitsnudel

(10) Patent No.: US 12,625,555 B1
(45) Date of Patent: May 12, 2026

(54) SYSTEMS FOR DETERMINING USER BREATH MOVEMENTS AND SYNCHRONIZING OUTPUT BASED ON BREATH MOVEMENTS

(71) Applicant: AMAZON TECHNOLOGIES, INC., Seattle, WA (US)

(72) Inventor: Ilia Vitsnudel, Even Yehuda (IL)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 1177 days.

(21) Appl. No.: 17/447,999

(22) Filed: Sep. 17, 2021

(51) Int. Cl.
| | |
|---|---|
| *G06F 3/01* | (2006.01) |
| *A61B 5/00* | (2006.01) |
| *A61B 5/024* | (2006.01) |
| *A61B 5/08* | (2006.01) |
| *G06V 40/20* | (2022.01) |

(52) U.S. Cl.
CPC .......... *G06F 3/015* (2013.01); *A61B 5/02416* (2013.01); *A61B 5/0816* (2013.01); *A61B 5/721* (2013.01); *A61B 5/7285* (2013.01); *G06V 40/23* (2022.01); *G06V 2201/07* (2022.01)

(58) Field of Classification Search
CPC ... G06F 3/015; A61B 5/02416; A61B 5/0816; A61B 5/721; A61B 5/7285; A61B 5/145; G06V 40/23; G06V 2201/07
See application file for complete search history.

(56) References Cited

U.S. PATENT DOCUMENTS

| | | | |
|---|---|---|---|
| 2012/0029361 A1* | 2/2012 | Addison ............ | A61B 5/02125 600/484 |
| 2019/0050985 A1* | 2/2019 | Den Brinker ........ | A61B 5/0261 |
| 2019/0209046 A1* | 7/2019 | Addison .............. | A61B 5/1135 |

* cited by examiner

*Primary Examiner* — Abid A Mustansir
(74) *Attorney, Agent, or Firm* — Lindauer Law, PLLC

(57) ABSTRACT

While a user performs an activity, a photoplethysmograph (PPG) sensor or other type of sensor is secured to the user's torso. Movement of the user's torso due to breathing changes the distance between the torso and the sensor, affecting an amplitude of a signal determined by the sensor. The amplitude is used to determine the position and rate of movement of the user's torso, which may indicate breath movements of the user. A camera acquires video data representing the user performing the activity. The position of the user's body and the portion of the activity being performed are determined based on the video data. An expected breath movement for the portion of the activity is determined. Corrective instructions or confirmations are output to the user based on the expected breath movement and the user's breath movement that was determined using the sensor.

14 Claims, 6 Drawing Sheets

100

TIME = T1

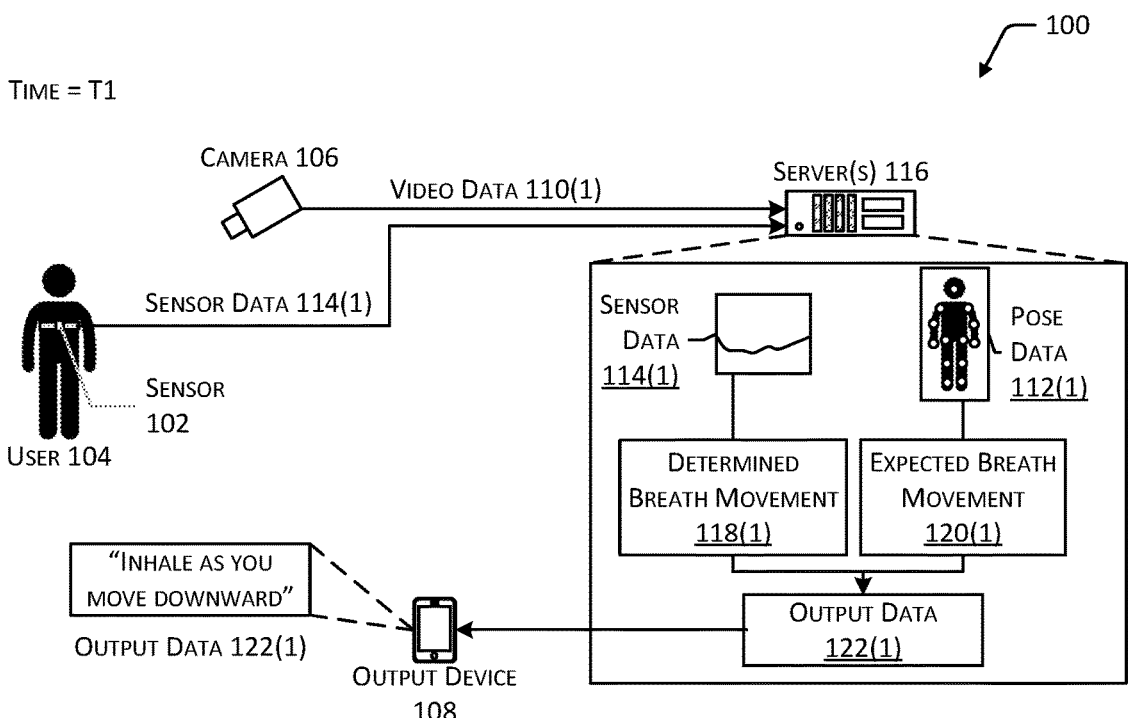

CAMERA 106
VIDEO DATA 110(1)
SERVER(S) 116

SENSOR DATA 114(1)

SENSOR
102

USER 104

SENSOR DATA 114(1)

POSE DATA 112(1)

DETERMINED BREATH MOVEMENT 118(1)

EXPECTED BREATH MOVEMENT 120(1)

"INHALE AS YOU MOVE DOWNWARD"

OUTPUT DATA 122(1)

OUTPUT DEVICE 108

OUTPUT DATA 122(1)

TIME = T2

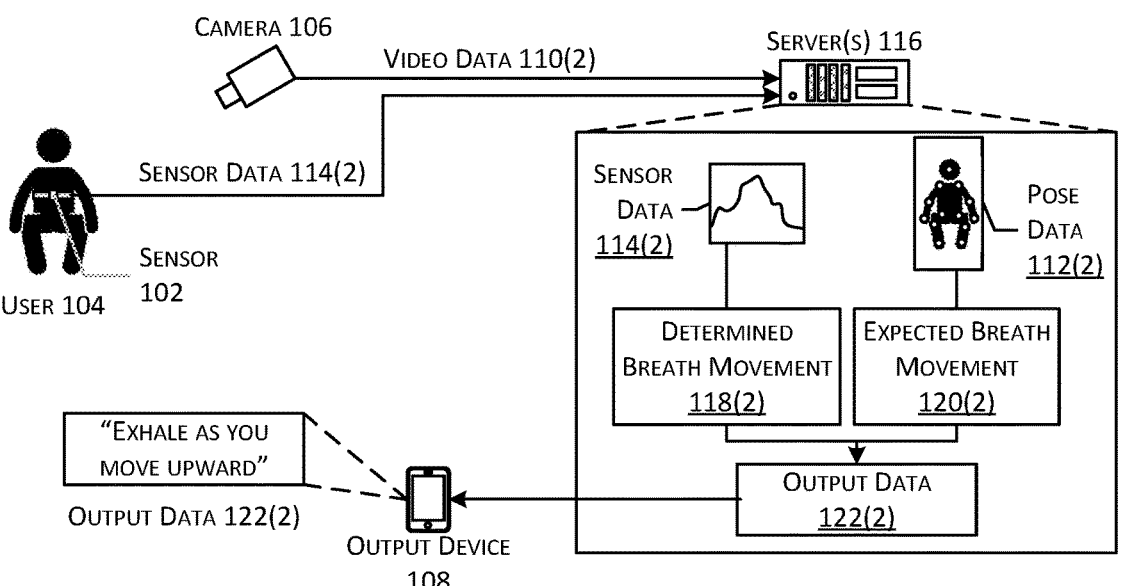

CAMERA 106
VIDEO DATA 110(2)
SERVER(S) 116

SENSOR DATA 114(2)

SENSOR
102

USER 104

SENSOR DATA 114(2)

POSE DATA 112(2)

DETERMINED BREATH MOVEMENT 118(2)

EXPECTED BREATH MOVEMENT 120(2)

"EXHALE AS YOU MOVE UPWARD"

OUTPUT DATA 122(2)

OUTPUT DEVICE 108

OUTPUT DATA 122(2)

FIG. 1

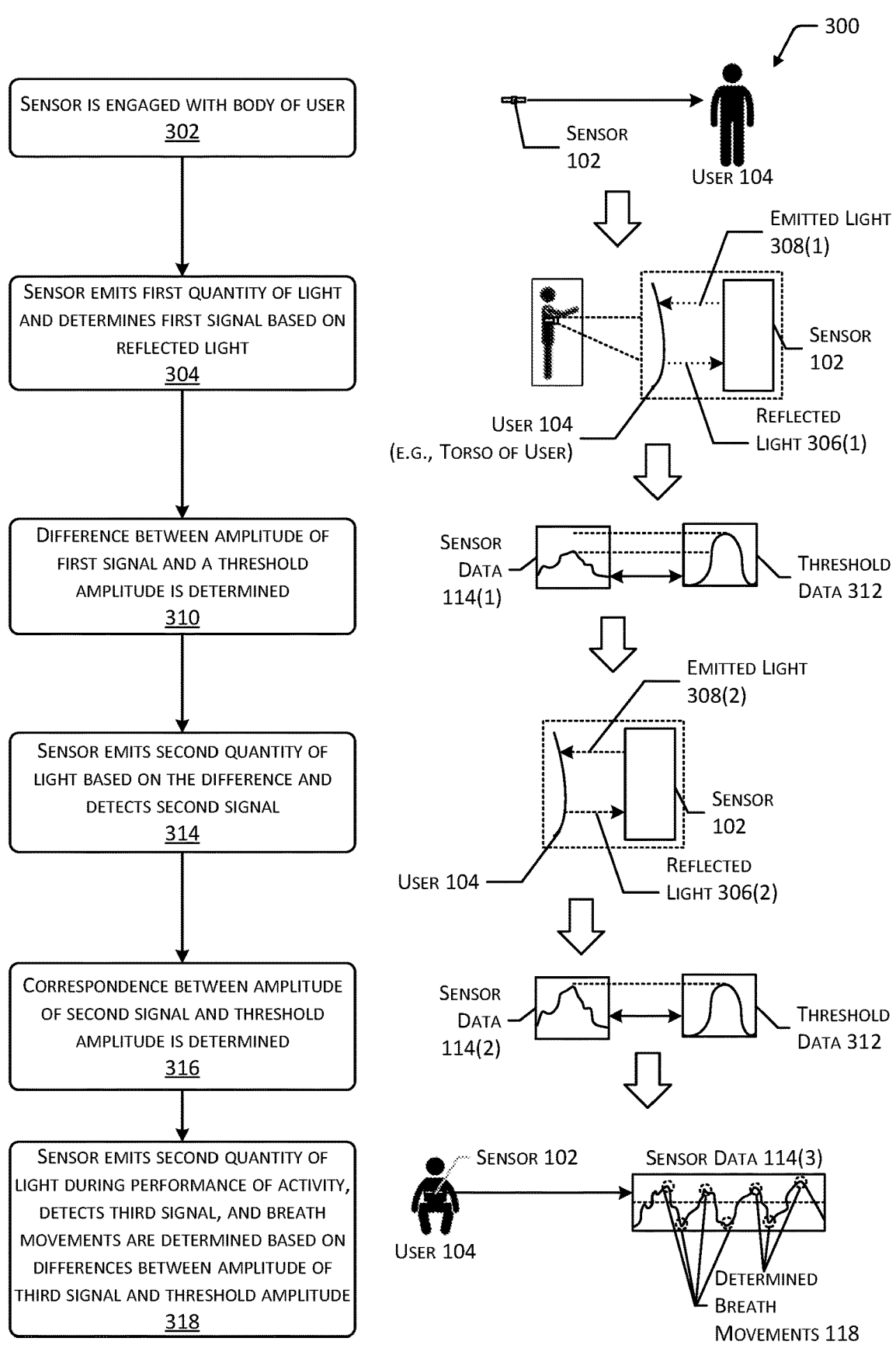

SENSOR IS ENGAGED WITH BODY OF USER
302

SENSOR EMITS FIRST QUANTITY OF LIGHT AND DETERMINES FIRST SIGNAL BASED ON REFLECTED LIGHT
304

DIFFERENCE BETWEEN AMPLITUDE OF FIRST SIGNAL AND A THRESHOLD AMPLITUDE IS DETERMINED
310

SENSOR EMITS SECOND QUANTITY OF LIGHT BASED ON THE DIFFERENCE AND DETECTS SECOND SIGNAL
314

CORRESPONDENCE BETWEEN AMPLITUDE OF SECOND SIGNAL AND THRESHOLD AMPLITUDE IS DETERMINED
316

SENSOR EMITS SECOND QUANTITY OF LIGHT DURING PERFORMANCE OF ACTIVITY, DETECTS THIRD SIGNAL, AND BREATH MOVEMENTS ARE DETERMINED BASED ON DIFFERENCES BETWEEN AMPLITUDE OF THIRD SIGNAL AND THRESHOLD AMPLITUDE
318

SENSOR 102    USER 104

EMITTED LIGHT 308(1)
SENSOR 102
REFLECTED LIGHT 306(1)
USER 104 (E.G., TORSO OF USER)

SENSOR DATA 114(1)    THRESHOLD DATA 312

EMITTED LIGHT 308(2)
SENSOR 102
REFLECTED LIGHT 306(2)
USER 104

SENSOR DATA 114(2)    THRESHOLD DATA 312

SENSOR 102
USER 104
SENSOR DATA 114(3)
DETERMINED BREATH MOVEMENTS 118

FIG. 3

SIGNAL
AMPLITUDE
404

DETERMINED BREATH
MOVEMENTS 118(1)

DETERMINED BREATH
MOVEMENTS 118(2)

DETERMINED BREATH
MOVEMENTS 118(3)

DETERMINED BREATH
MOVEMENTS 118(2)

DETERMINED BREATH
MOVEMENTS 118(3)

SECOND SENSOR DATA 114(2)
(E.G., FROM STRAIN GAUGE)

DETERMINED BREATH
MOVEMENTS 118(1)

T1
(BREATHING
NORMALLY)

T2
(BEGIN HOLDING
BREATH)

T3
(BEGIN PERFORMING
ACTIVITY)

TIME
402

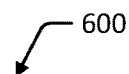

600

COMPUTING DEVICE
602

POWER SUPPLY
604

PROCESSOR(S)
606

CLOCK(S)
608

COMMUNICATION
INTERFACE(S) 610

I/O INTERFACE(S)
612

NETWORK
INTERFACE(S) 614

I/O DEVICE(S) 616

MEMORY 618

OPERATING SYSTEM MODULE
620

COMMUNICATION MODULE
624

IMAGE ANALYSIS MODULE
202

ACTIVITY MODULE 204

SIGNAL ANALYSIS MODULE 208

BREATH ANALYSIS MODULE 212

OUTPUT MODULE 216

OTHER MODULE(S)
626

DATA STORE 622

VIDEO DATA 110

POSE DATA 112

SENSOR DATA 114

OUTPUT DATA 122

ACTIVITY DATA 206

BREATH DATA 214

PRESENTATION DATA 218

THRESHOLD DATA 312

OTHER DATA 628

FIG. 6

SYSTEMS FOR DETERMINING USER BREATH MOVEMENTS AND SYNCHRONIZING OUTPUT BASED ON BREATH MOVEMENTS

BACKGROUND

Video and audio instruction may be used to assist a user when performing a variety of activities, such as fitness exercises. In some cases, input from cameras and other sensors may be used to determine characteristics of the user's performance, which may affect the specific instruction that is presented. Determining the breath movements of the user during performance of the activity may provide information regarding the user's performance and useful output that may be presented. However, user motion during various activities may cause many methods for determining the user's breath movements to be inaccurate, or in some cases impossible.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

FIG. 1 depicts an implementation of a system for determining breath movements based on signals from a sensor and determining outputs based on expected breath movements.

FIG. 3 is a diagram depicting an implementation of a process for calibrating a sensor based on a threshold amplitude for signals and using deviations from the threshold amplitude to determine breath movements of a user.

FIG. 6 is a block diagram depicting an implementation of a computing device within the present disclosure.

Figure 2:
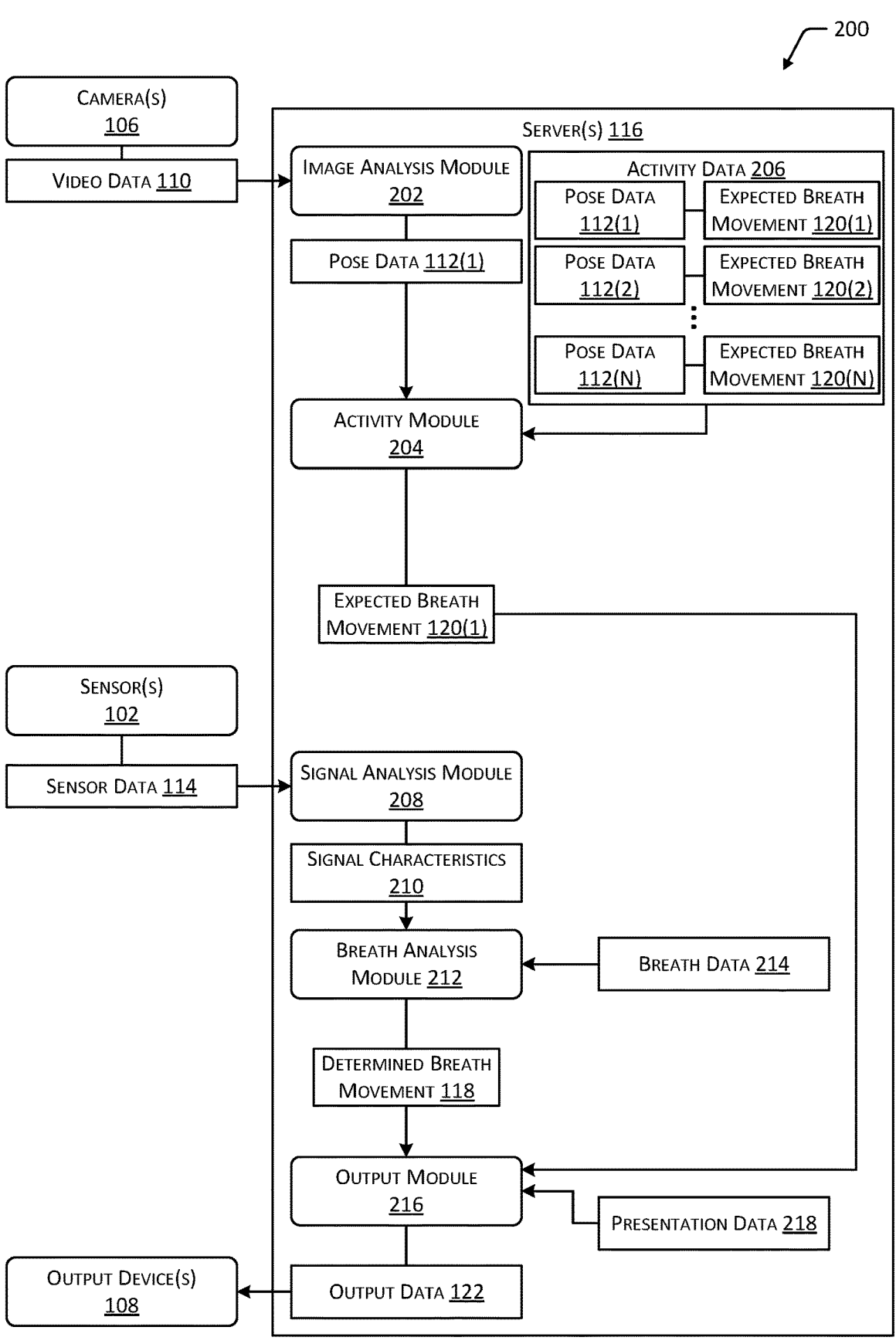
FIG. 2 is a block diagram depicting an implementation of a system for determining breath movements based on sensor data from one or more sensors and determining outputs associated with the breath movements.

While implementations are described in this disclosure by way of example, those skilled in the art will recognize that the implementations are not limited to the examples or figures described. It should be understood that the figures and detailed description thereto are not intended to limit implementations to the particular form disclosed but, on the contrary, the intention is to coverall modifications, equivalents, and alternatives falling within the spirit and scope as defined by the appended claims. The headings used in this disclosure are for organizational purposes only and are not meant to be used to limit the scope of the description or the claims. As used throughout this application, the word "may" is used in a permissive sense (i.e., meaning having the potential to) rather than the mandatory sense (i.e., meaning must). Similarly, the words "include", "including", and "includes" mean "including, but not limited to".

DETAILED DESCRIPTION

Video and audio instruction may be used to assist users when performing various activities. For example, a video may depict an instructor performing a fitness exercise while providing verbal instruction. A user may attempt to perform the exercise by duplicating the visible movements of the instructor and following audible instructions. In some cases, data regarding performance of an activity by a user may be acquired and used to provide feedback or additional instruction. For example, a user may perform a fitness exercise within a field of view of a camera, and video data acquired by the camera may be used to determine the positions and movements of the user's body. The determined positions and movements may be compared to known positions and movements that represent correct performance of the activity, and output may be presented that indicates correct or incorrect performance, such as encouragement, corrective instruction, a score or other type of rating, and so forth.

In some cases, proper performance of an activity may include use of certain breath movements (e.g., specific times for a user to inhale, exhale, hold their breath, rates of inhalation and exhalation (e.g., velocity of airflow), breathing rates, volume of air to inhale and exhale, and so forth). In other cases, certain breath movements may facilitate performance of an activity, such as timing inhalation and exhalation to coincide with certain portions of a weight training exercise or maintaining a target breath rate while performing aerobic exercise. However, determination of breath movements during performance of certain activities may be subject to inaccuracy. For example, video data acquired using a camera may be used to determine movements of a user's chest and abdomen that may indicate breathing, however, if the activity performed by the user involves significant motion, determination of the smaller movements of the chest and abdomen that correspond to breathing may be inaccurate, or determination of such movements may not be possible. Similarly, an accelerometer or other motion sensor may detect movements of a user's chest and abdomen that correspond to breathing when the user is reasonably still, but when the user is performing an activity that involves significant motion, determination of breath movements using an accelerometer may be impossible, or subject to significant inaccuracy. Various types of microphones or detectors placed near a user's mouth may be used to detect breath movements, however, wearing of such equipment during performance of some activities may be cumbersome, and determinations using these types of detectors may be subject to inaccuracy during performance of activities that include significant movement or when ambient noise is present.

Described in this disclosure are techniques for determining breath movements of a user during performance of an activity using the strength (e.g., amplitude) of signals determined using a wearable sensor. Determination of user breath movements may improve a user's experience when attempting to perform an activity by enabling instructive or corrective output to be presented, that is specific to the determined position of the user's body or the expected position of the user's body based on the activity that is performed. A wearable device used to determine breath movements of a user may include a photoplethysmograph (PPG) sensor, or another type of sensor having one or more light sources that emit light, or a sensor that emits one or more other types of signals that may be reflected by the body of a user. The sensor may be engaged with a portion of the user's body that is suitable for determining breath movements, such as the chest or abdomen of the user, in a manner that constrains at least a portion of the relative motion between the sensor and the user's body that may be caused by performance of the activity. For example, a strap or other type of fastener may be used to secure a sensor to the user's body in a position such that light, or other signals, emitted by the sensor may be at least partially reflected by the user's body, and the reflected light or other signal may be detected by the sensor. The strap or other type of fastener may prevent at least a portion of the relative motion between the sensor and the user's body that would otherwise occur due to performance of the activity of the user, while enabling movements of the user's chest or abdomen relative to the sensor to be detected. In some implementations, multiple sensors may be engaged with respective portions of the user's body, such as a first sensor positioned on the user's chest and a second sensor on the abdomen.

As the user performs the activity, data from the sensor may be used to determine characteristics of the user or of performance of the activity, based on the type of sensor used. For example, a PPG sensor may emit light using one or more light sources. A detector associated with the PPG sensor may detect light that is at least partially reflected, diffused, fluoresced, or otherwise interacts with the user's body in a manner that may be detected by the detector. Based on characteristics of the reflected light, one or more physiological values of the user may be determined. In addition to, or independent of, characteristics of the signal that are determined by the sensor, the signal may also be used to determine breath movements of the user based on the amplitude of the signal. As the user breathes during performance of an activity, the distance or orientation of the torso (e.g., chest or abdomen) of the user relative to the sensor may change, or other characteristics of the user's body caused by movement of the torso or the intake or exhalation of breath may cause a change in the amplitude or another characteristic of the signal. For example, the chest of the user may move closer to a light source or detector of an engaged sensor when the user inhales, and move farther from the light source or detector when the user exhales. The amplitude of the determined signal may vary inversely relative to the distance or other characteristic of the user's body affected by the breath movement. Based on the amplitude of the signal determined by the sensor, the breath movements of the user may be determined. The determined breath movements may include times when the user inhales and exhales, as well as a breath rate, and a rate at which the user inhales or exhales, which may indicate whether the user is breathing lightly, breathing heavily, gasping, a volume of air that is inhaled or exhaled, and so forth. Because the sensor is secured to the user's body using a strap or other type of fastener, and the amplitude of the signal, or other characteristics of the signal that may be relatively unaffected by user movement, are used to determine breath movements, the effect of motion of the user during performance of the activity on the accuracy of the signal is reduced.

In some implementations, one or more additional sensors may be used to improve the accuracy of the determined breath movements. For example, the strap or other fastener that engages the sensor to the user's body may include a strain gauge, which may determine a signal indicative of movement of the strap that may indicate the breath movements of the user. As another example, a camera may be used to acquire video data representing the user performing the activity. The video data may be analyzed to determine one or more poses of the user. A pose may be represented by a set of points, each point representing the location and orientation of a body part of the user, such as positions of the user's knees, feet, hips, head, and so forth. For example, a pose may include one or more points from which the position of a user's chest or abdomen may be determined, which may be indicative of a breath movement. Use of multiple types of sensors to determine breath movements may improve the precision of the determination, reduce the effect of noise on individual signals, and so forth. In some implementations, the particular sensors that are used to determine the breath movements may be selected based on characteristics of the activity. For example, certain signals from sensors may be used, disregarded, or weighted differently if a selected activity includes user motion that is greater than a threshold amount, or if motion of the user detected using an accelerometer or other type of sensor exceeds the threshold amount.

In some implementations, a camera may be used to acquire video data that represents the user performing the activity while the PPG sensor, or other type of sensor, determines signals from which breath movements may be determined. One or more poses of the user may be determined based on the video data, and the determined poses may be used to determine a portion of the activity that is being performed by the user. An expected breath movement that corresponds to the determined portion of the activity may be determined based on activity data that associates expected breath movements with portions of the activity. For example, activity data may indicate that during a squat exercise, the expected breath movements include inhaling while moving in a downward direction, and exhaling while moving in an upward direction. Based on correspondence between the expected breath movement for the determined portion of the activity and the breath movement of the user determined using the sensor, an output may be determined. For example, a user may be provided with corrective instruction if the user's breath movement differs from the expected breath movement, confirmation if the user's breath movement corresponds to the expected breath movement, and so forth. In some cases, output may be presented as the user performs the activity. In other cases, output may be presented after the user completes the activity, such as by presenting a score, rating, or instructional feedback based on correspondence between the user's breath movements and the expected breath movements during performance of the activity. Providing useful instruction regarding breath movements during or after performance of an activity may improve a user experience by enabling a user to perform proper breath movements during a specific portion of an activity where a breath movement may improve or facilitate performance of the activity. In cases where breath movements of a user may not be measured, or may be impossible to measure accurately, use of techniques described herein may add an additional type of useful output that may be presented, in addition to other information determined during performance of an activity by a user.

In some implementations, before the sensor is used to acquire signals indicative of breath movement, the sensor may emit signals to cause calibration of the sensor. For example, a PPG sensor engaged to the body of a user may emit a first quantity or intensity of light before acquiring signals indicative of breath movements or signals to determine PPG measurements. The sensor may determine one or more characteristics of the reflected light, then increase or decrease the quantity or intensity of emitted light to cause the reflected light to correspond to one or more threshold characteristics. This process may be performed iteratively, such as by slightly increasing or decreasing the quantity or intensity of emitted light until the reflected light has one or more characteristics that correspond to the threshold characteristic(s). For example, the resulting quantity or intensity of emitted light may be selected to cause the amplitude of a signal indicative of reflected light to be within a threshold value of a target amplitude that is suitable for acquisition of PPG measurements. As a result, signals determined using the PPG sensor may have a known average amplitude, and deviations from the known average amplitude may be used to determine breath movements of the user.

Implementations described herein may therefore enable breath movements of a user to be accurately determined, and in some cases compared to expected breath movements for an activity, during performance of an activity that includes motion of the user. Use of a PPG sensor, or another type of sensor for which the amplitude of a signal may be used, independent of the physiological values associated with the signal, to determine breath movements may reduce the effect of user motion on the accuracy of the determined breath movements. Determination of accurate breath movements using a sensor, in combination with determining the current pose or portion of an activity performed by a user, may enable user breath movements to be compared to expected breath movements, enabling relevant contemporaneous output to be provided, or relevant output to be provided after completion of the activity. Instructive or corrective output may then be presented to facilitate or improve performance of the activity by the user, resulting in an improved user experience.

FIG. 1 depicts an implementation of a system 100 for determining breath movements based on signals from a sensor 102 and determining outputs based on expected breath movements. For example, based on determined breath movements of a user 104, video or audio outputs that include instructive or corrective output may be presented that correspond to video output presented to the user 104 or video input received from the user 104. At a first time T1, a user 104 may perform an activity within a field of view of one or more cameras 106. In some implementations, an output device 108 may present instructional output, such as video or audio instructions for performance of the activity. For example, an activity may include a fitness exercise, and the output device 108 may present a video representing an instructor performing the fitness exercise while providing verbal instruction, while the user 104 attempts to perform the fitness exercise by achieving the positions and movements indicated in the video. As the user 104 performs the activity, the camera 106 may acquire video data 110(1) that represents performance of the activity by the user 104. The video data 110(1) may be processed, such as through use of one or more pose estimation algorithms, to determine pose data 112(1) that indicates the position of the body of the user 104 in one or more frames of the video data 110(1). For example, a pose may be represented by a set of points, each point representing the location and orientation of a body part of the user 104.

During performance of the activity, some of the movements performed by the user 104 may include breath movements, such as inhalation, exhalation, holding the breath, and so forth. However, due to motion of the user 104 during performance of the activity, breath movements determined based on the pose data 112(1) may be subject to inaccuracy. For example, significant or rapid movement of the body of the user 104 while performing a fitness exercise may cause subtle movements in the chest or abdomen of the user 104, that are associated with breathing, to be difficult or impossible to detect based on the acquired video data 110(1). To determine breath movements of the user 104, one or more sensors 102 may be secured to the body of the user 104 to acquire sensor data 114(1). For example, a sensor 102 may include a device that emits light, or other signal, toward the body of the user 104. In some implementations, the sensor 102 may include a photoplethysmograph (PPG) sensor. For example, a PPG sensor may emit light from one or more light sources and determine physiological characteristics of the user 104 based on the characteristics of detected light that is reflected, refracted, diffused, or otherwise affected by the skin or other parts of the body of the user 104. In other implementations, a sensor 102 may emit other types of signals that may be reflected or otherwise affected by the body of the user 104. For example, the sensor 102 may emit a radio signal, detect an impedance change, detect a capacitance change, and so forth. In still other implementations, a sensor 102 may detect signals emitted by the body of the user 104, such as infrared signals, and the sensor 102 may not necessarily emit a signal.

The sensor 102 may be secured to the body of the user 104 using one or more straps or other types of fasteners that reduce movement of the sensor 102 relative to the body as the user 104 moves during performance of the activity. As a result, the effect of the movement of the user 104 during performance of the activity on the distance or orientation of the sensor 102 relative to the body of the user 104 may be minimized. Therefore, changes in the distance between the sensor 102 and the body of the user 104, or the orientation of the sensor 102 relative to the body of the user 104, that occur may be primarily caused by movement of the torso of the user 104 that is associated with breathing. In some implementations, breath movements of the user 104 may be determined based on the amplitude of the signal represented by the sensor data 114(1), independent of other physiological values, such as PPG measurements, that may be determined based on the sensor data 114(1). For example, the amplitude of a signal represented by the sensor data 114(1) may be affected by the distance between the torso of the user 104 and a light source or detector of the sensor 102. In other implementations, other characteristics of the signal, such as a frequency, strength, electrical resistance, electrical impedance, or rate of change of an amplitude, frequency, or other characteristic may be used in addition to or in place of the amplitude of the signal.

FIG. 1 depicts one or more servers 116 receiving the video data 110(1) and sensor data 114(1). However, in other implementations, a user device, such as the output device 108 or another computing device in an environment with the user 104, may be used to receive and process the video data 110(1) and sensor data 114(1). In still other implementations, a combination of computing devices in an environment with the user 104 and remote computing devices, such as servers 116, may be used. The server(s) 116, or another computing device, may determine a determined breath movement 118(1) based on the amplitude, and in some implementations one or more other characteristics, of the signal represented by the sensor data 114(1). For example, a distance between the torso of the user 104 and the sensor 102 may vary inversely relative to the amplitude of the signal, such that an increase in amplitude represents an inhalation breath movement (which may move the torso of the user 104) closer to the sensor 102, while a decrease in amplitude may represent an exhalation breath movement (which may move the torso of the user 104) farther from the sensor 102. The rate at which the amplitude of the signal changes may represent an intensity of a breath movement. For example, a rapid increase in amplitude may represent a gasp or other rapid intake of air, while multiple rapid increases and decreases in amplitude may represent hard breathing. Additionally, the rate at which increases and decreases in amplitude occur may be used to determine a breathing rate of the user 104, a volume of air inhaled or exhaled, and so forth.

The server(s) 116 or other computing device may also determine pose data 112(1) based on the video data 110(1) acquired using the camera 106. Based on the pose data 112(1) a portion of an activity being performed by the user 104 may be determined. The server(s) 116 or other computing device may determine an expected breath movement 120 based on the determined portion of the activity. For example, the server(s) 116 may access activity data that indicates expected breath movements 120(1) for one or more portions of an activity. Based on correspondence between the determined breath movement 118(1) and the expected breath movement 120(1), the server(s) 116 or other computing device may determine output data 122(1). Output data 122(1) may include a visible or audible instruction or other type of feedback indicative of differences or correspondence between the determined breath movement 118(1) and expected breath movement 120(1). For example, FIG. 1 depicts the user 104 in a generally upright position at the first time T1, while the output data 122(1) includes an instruction to inhale as the user 104 moves in a downward direction. In other implementations, the expected breath movement 120 (1) may be determined based on output that is presented using the output device 108. For example, the output may include video or audio instruction indicating a particular portion of an activity, and the expected breath movement 120(1) that corresponds to the portion of the activity associated with the output may be determined and used to determine output data 122(1).

At a second time T2, the user 104 may continue performance of the activity, such as by moving to a different position. The camera 106 may acquire video data 110(2) indicative of the movement and position of the user 104. The server(s) 116 or another computing device may determine pose data 112(2) that represents the position of the user 104 in one or more frames of the video data 110(2), and may determine an expected breath movement 120(2) based on the pose data 112(2). The sensor 102 may acquire sensor data 114(2), such as by emitting light or another type of signal toward the body of the user 104 and detecting the reflected light or other type of signal. The server(s) 116 or other computing device may determine a determined breath movement 118(2) based on an amplitude, and in some implementations one or more other characteristics, of the signal represented by the sensor data 114(2). The server(s) 116 or other computing device may determine output data 122(2) based on correspondence between the determined breath movement 118(2) and expected breath movement 120(2), which may cause an output to be presented by the output device 108. For example, at the second time T2, FIG. 1 depicts the output device 108 presenting an instruction to exhale as the user 104 moves in an upward direction. In other implementations, output may be presented after a user 104 has completed an activity in addition to or in place of presentation during performance of the activity.

FIG. 2 is a block diagram 200 depicting an implementation of a system for determining breath movements based on sensor data 114 from one or more sensors 102 and determining outputs associated with the breath movements. As described with regard to FIG. 1, one or more cameras 106 may acquire video data 110 that represents a user 104 performing an activity within a field of view of the camera(s) 106. In some implementations, one or more servers 116 may receive and process the video data 110. In other implementations, one or more other computing devices, such as a computing device in an environment with the user 104, may receive and process the video data 110. For example, a smartphone that includes one or more cameras 106 may be used to acquire and process video data 110, and use of one or more servers 116 or other separate computing devices may be omitted. In other implementations, a combination of one or more computing devices in an environment with the user 104 and one or more separate computing devices, such as servers 116, may be used. As such, the functions described with regard to the server(s) 116 shown in FIG. 2 may be performed using any number and any type of computing devices.

An image analysis module 202 associated with the server(s) 116 may receive the video data 110 and determine pose data 112(1) based on the video data 110. For example, the image analysis module 202 may use one or more pose estimation algorithms to determine one or more poses of the user 104 based on one or more frames of video data 110. In some implementations, the image analysis module 202 may include one or more object recognition or segmentation algorithms to identify portions of frames of video data 110 in which the user 104 is visible. An object recognition algorithm may determine portions of a frame of video data 110 that correspond to particular body parts of the user 104. The pose data 112(1) may represent the determined positions of parts of the user's body as a set of points. For example, each point may correspond to the location of a particular body part of the user 104. The locations and orientations of one or more points may be constrained by the location of one or more other points based on a set of rules. For example, the location of a point representing a location of the user's elbow may be constrained relative to a point representing a location of the user's shoulder. In some implementations, each point of a pose may associate an identifier of the point with a particular location or orientation of the point. In some implementations, data regarding a point may also indicate movement of the point, a confidence value associated with the location of the point, and so forth. In some implementations, the pose data 112(1) may also include segmentation information, shape information, information regarding a three-dimensional position of a user 104 or other object (such as information determined using a depth (e.g., RGB-D) camera), and so forth that may indicate portions of video data 110 that include a user 104, a background, one or more other objects, and so forth.

An activity module 204 associated with the server(s) 116 may determine an expected breath movement 120(1) based on the determined pose data 112(1) and activity data 206 that associates expected breath movements 120 with portions of an activity represented by pose data 112. For example, an activity may be associated with movement of the user 104 between multiple positions. The activity data 206 may associate one or more positions, represented as pose data 112, with a corresponding expected breath movement 120. Continuing the example, the activity data 206 may associate an upward movement during a squat exercise with an exhalation breath movement, a downward movement during the squat exercise with an inhalation breath movement, and so forth. FIG. 2 depicts the activity data 206 associating first pose data 112(1) representing a first portion of an activity with a first expected breath movement 120(1), second pose data 112(2) with a second breath movement 120(2), and any number of additional pose data 120(N) with corresponding expected breath movements 120(N). Based on the activity data 206, the activity module 204 may determine a portion of the activity, represented by pose data 112, that most closely corresponds to the pose data 112(1) determined using the image analysis module 202, and a particular expected breath movement 120(1) that is associated with the determined portion of the activity. In other implementations, the activity data 206 may associate particular portions of video or audio output that may be presented to a user 104, or particular poses that may be determined based on a video output, with corresponding expected breath movements 120. For example, an expected breath movement 120 may be determined based on a portion of an activity presented using an output device 108 independent of, or in addition to, a determined pose of the body of the user 104.

As the user 104 performs the activity, one or more sensors 102 may determine sensor data 114. For example, a sensor 102 may include a PPG sensor or other type of sensor that emits light, or another detectable signal. The sensor data 114 may represent a signal indicative of detected light, or other type of signal, that is at least partially reflected or otherwise affected by the body of the user 104. As such, characteristics of the sensor data 114 may be used to determine a position of a portion of the body of the user 104 relative to a sensor 102. For example, a sensor 102 secured to a chest or abdomen of the user 104 may be used to determine the position of the chest or abdomen based on an amplitude of the signal detected by the sensor 102, in some cases in addition to determining one or more physiological values, and breath movements of the user 104 may be determined based on the amplitude of the signal. A signal analysis module 208 associated with the server(s) 116 may determine one or more signal characteristics 210 based on the sensor data 114. For example, a signal characteristic 210 may include an amplitude of a received signal, which may represent the strength or intensity of reflected light detected by a detector of the sensor 102. In some implementations, one or more other types of sensors 102, such as strain gauges, accelerometers, position sensors, cameras 106, and so forth, may also be used to determine signals that may indicate the position of one or more portions of the body of the user 104. For example, use of multiple sensors 102 may improve precision and reduce noise or uncertainty when determining breath movements of the user 104.

A breath analysis module 212 associated with the server(s) 116 may determine a determined breath movement 118 based on the signal characteristics 210. In some implementations, the determined breath movement 118 may be determined based on breath data 214, which may associate signal characteristics 210 with breath movements. For example, the breath data 214 may include one or more algorithms, rules, and so forth that correlate values for signal amplitude with particular breath movements, such as inhalation and exhalation, rules or algorithms for determining amounts of air inhaled or exhaled, or rates of inhalation and exhalation based on a rate of change of an amplitude or other characteristic, and so forth. Continuing the example, the breath data 214 may indicate deviations from a known or average signal amplitude that correspond to an inhalation breath movement, an exhalation breath movement, and so forth. The breath data 214 may also indicate signal characteristics 210, such as rates of change in signal amplitude, that correspond to particular types of breathing, such as rapid or hard breathing, holding of breath, certain breathing rates, and so forth.

An output module 216 associated with the server(s) 116 may determine output data 122 based on correspondence between the determined breath movement 118 and the expected breath movement 120(1). For example, if the determined breath movement 118 differs from the expected breath movement 120(1) by at least a threshold value, the output data 122 may include an instruction, feedback, score, rating, and so forth indicative of the difference. If the determined breath movement 118 corresponds to the expected breath movement 120(1) within a threshold value, the output data 122 may be omitted, or the output data 122 may include a confirmation, feedback, score, or rating indicative of the correspondence. In some implementations, presentation data 218 may be used to control the output data 122 that is determined and sent to an output device 108. For example, presentation data 218 may include one or more rules, algorithms, threshold values, and so forth that may be used to determine differences between the determined breath movement 118 and the expected breath movement 120(1), outputs that correspond to the differences, formats for presentation of the outputs, times for presentation of the outputs, and so forth. Continuing the example, the presentation data 218 may indicate particular outputs for presentation after the completion of an activity by the user 104, while other outputs may be presented during performance of the activity by the user 104.

FIG. 3 is a diagram 300 depicting an implementation of a process for calibrating a sensor 102 based on a threshold amplitude for signals and using deviations from the threshold amplitude to determine breath movements of a user 104. At 302, a sensor 102 is engaged with a body of a user 104. In some implementations, the sensor 102 may include a PPG sensor. However, in other implementations, the sensor 102 may include any type of device that emits light, or another type of signal that may be at least partially reflected, diffused, refracted, fluoresced, or otherwise affected by an interaction with the body of a user 104 then detected using one or more detectors. In still other implementations, the sensor 102 may include a device that detects a signal emitted by the body of the user 104, such as by detecting an infrared signal. Engagement of the sensor 102 with the user 104 may include securing the sensor 102 to at least a portion of the body of the user 104 using one or more fasteners, such as a strap. For example, a PPG sensor 102 may be strapped to the body of the user 104 such that the sensor 102 is adjacent to a chest or abdomen of the user 104 and constrained from movement relative to the body of the user 104 that may be caused by motion during performance of an activity. In some implementations, multiple sensors 102 may be engaged with the user 104. For example, a strap that secures a sensor 102 to the chest of the user 104 may also include a strain gauge that may be used to determine signals indicative of deflection of the strain gauge, which may be due to breath movements of the user 104. As another example, multiple PPG sensors, or other types of sensors 102 that emit light or other signals, may be secured to different portions of the body of the user 104, such as by securing a first sensor 102 to a chest of the user 104 and a second sensor 102 to the abdomen of the user 104. In still other implementations, sensors 102 may not necessarily be secured directly to the body of the user 104, but may be positioned at a location that enables signals emitted by the sensor(s) 102 to be reflected or to otherwise interact with the body of the user 104, prior to detection of a signal after an interaction.

At 304, the sensor 102 may emit a first quantity of light, and a first signal may be determined based on reflected light 306(1). For example, a PPG sensor 102, or another type of sensor 102, may include one or more light sources, such as light emitting diodes (LEDs). At least a portion of the light sources of the sensor 102 may be actuated to cause the first quantity of light to be emitted. In some implementations, a quantity of light sources may be actuated to control the quantity of light that is emitted. In other implementations, an amount of power provided to the light source(s) may be used to control the quantity of light. In still other implementations, an intensity of the emitted light may be controlled using the light sources or another portion of the sensor 102 to control the output of the light sources. The light sources may generate emitted light 308(1), at least a portion of which may be emitted toward the body of the user 104, such as toward the user's torso. The body of the user 104 may reflect at least a portion of the emitted light 308(1). Reflected light 306(1) may be detected by one or more detectors associated with the sensor 102. For example, the sensor 102, or a computing device in communication with the sensor 102, may determine sensor data 114(1) that represents a signal indicative of the reflected light 306(1). In other implementations, other types of signals in addition to, or in place of, light may be emitted by the sensor 102 and at least partially reflected or otherwise affected by the body of the user 104, such as electromagnetic signals.

At 310, a difference between an amplitude of the first signal and a threshold amplitude may be determined. For example, a signal represented by the first sensor data 114(1) may be analyzed to determine an amplitude or one or more other signal characteristics 210. The determined amplitude or other signal characteristics 210 may be compared to one or more threshold values for amplitude or other signal characteristics 210, represented by threshold data 312. In other implementations, the threshold data 312 may represent a threshold signal, and the signal represented by the first sensor data 114(1) may be compared to the threshold signal to determine one or more differences. In some implementations, the threshold data 312 may also include one or more threshold values indicative of a magnitude of a difference between the sensor data 114(1) and the threshold data 312 that may constitute a significant difference or a similarity between the amplitude or other signal characteristics 210.

At 314, the sensor 102 may emit a second quantity of light based on the difference(s) and detect a second signal. In other implementations, other types of signals in addition to, or in place of, light may be emitted. For example, if the amplitude represented by the first sensor data 114(1) is greater than a threshold amplitude by at least a threshold value, the second quantity of light may be less than the first quantity of light. If the amplitude represented by the first sensor data 114(1) is less than the threshold amplitude by at least a threshold value, the second quantity of light may be greater than the first quantity of light. For example, FIG. 3 depicts the first sensor data 114(1) representing a signal having an amplitude less than a threshold amplitude represented by the threshold data 312. Therefore, the sensor 102 may emit a second quantity of emitted light 308(2) greater than the first quantity of emitted light 308(1), which may affect the characteristics of the reflected light 306(2) detected by the sensor 102. For example, the amplitude of a signal that represents the reflected light 306(2) may be greater than the amplitude of the signal represented by the first sensor data 114(1).

At 316, correspondence between the amplitude of the second signal represented by the second sensor data 114(2) and the threshold amplitude represented by the threshold data 312 is determined. In other implementations, correspondence between one or more other signal characteristics 210 and threshold values for the characteristics may be determined. Due to the second quantity of light being selected based on the difference between the amplitude of the first signal and the threshold amplitude, the amplitude of the second signal may be closer to the threshold amplitude than the amplitude of the first signal. However, if the amplitude of the second signal differs from the threshold amplitude by at least a threshold value, the actions indicated at 314 and 316 may be repeated until correspondence between an amplitude of a determined signal and the threshold amplitude is determined to be within a threshold value. For example, the quantity of light or other type of signal emitted by a sensor 102 may be incrementally increased or decreased based on the determined difference between a detected signal and a threshold characteristic until the determined characteristic(s) of a signal corresponds to threshold data 312.

At 318, the sensor 102 may emit the second quantity of light during performance of an activity by the user 104. The sensor 102 may detect a third signal during performance of the activity. Breath movements of the user 104 may be determined based on differences between the amplitude of the third signal and the threshold amplitude. For example, the threshold amplitude may include an average signal amplitude associated with acquisition of signals by the sensor 102, such as a signal amplitude sufficient for determining physiological values using a PPG sensor. Continuing the example, the threshold amplitude may be a value independent of the breath movements of the user 104. However, due to the placement of the sensor 102 on the body of the user 104, such as on the torso, breath movements of the user 104 may cause the amplitude of signals determined using the sensor 102 to change, such as by changing a distance or orientation of the sensor 102 relative to the body of the user 104 or otherwise affecting the manner in which the detected signal is affected by the body of the user 104. Therefore, differences between the amplitude of the determined signal and the threshold amplitude may indicate breath movements of the user 104. Continuing the example, at times when the amplitude of a signal is greater than the threshold amplitude, this may indicate that the body of the user 104 is closer to a detector or light source of the sensor 102, which may be indicative of an inhalation breath movement. Times when the amplitude of the signal is less than the threshold amplitude may correspond to times that the body of the user 104 is farther from the detector or light source of the sensor 102, which may indicate an exhalation breath movement. For example, FIG. 3 depicts third sensor data 114(3) representing a signal determined while an activity is performed by the user 104. The signal may include one or more peaks (e.g., areas where the amplitude is greater than the threshold amplitude by at least a threshold value) and troughs (e.g., areas where the amplitude is less than the threshold amplitude, or the peak amplitude, by at least a threshold value). In some cases, the amount by which the amplitude of a portion of a signal deviates from a threshold amplitude may indicate a rate at which air is inhaled or exhaled, an amount (e.g., volume) of air inhaled or exhaled, and so forth. Additionally, in some cases, the rate at which the amplitude of the signal changes may indicate a rate at which air is inhaled or exhaled, a breath rate, and so forth.

Figure 4:
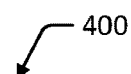
FIG. 4 is a graph depicting example signals determined using multiple sensors over a period of time.

FIG. 4 is a graph 400 depicting example signals determined using multiple sensors 102 over a period of time. The horizontal axis 402 of the graph 400 represents time, while the vertical axis 404 of the graph 400 represents the amplitude of the determined signals. As described with regard to FIGS. 1-3, in some implementations, data may be determined using multiple sensors 102. For example, a first PPG sensor may be positioned near a chest of a user 104 while a second PPG sensor is positioned near an abdomen of the user 104. In other cases, different types of sensors 102 may be used. For example, a first sensor 102 may include a PPG sensor secured to the torso of a user 104 using a strap, while a second sensor 102 includes a strain gauge associated with the strap. Use of multiple signals determined using multiple sensors 102 may improve precision of determined breath movements 118 and reduce noise.

In the graph 400 shown in FIG. 4, first sensor data 114(1) may represent an example first signal determined using a PPG sensor. For example, a PPG sensor may emit light toward a body of the user 104, which may reflect at least a portion of the light. The PPG sensor may detect the reflected light and determine sensor data 114(1) that represents the detected signal. The signal may have one or more signal characteristics 210, which in some cases may be used to determine one or more physiological values associated with the user 104, such as PPG measurements. One signal characteristic 210 of the signal may include an amplitude of the signal. The amplitude of the signal may be used to determine breath movements of the user 104 based on the manner in which the body of the user 104 affects the amplitude of the signal during different breath movements. As one example, a greater amplitude may represent a time when a detector or light source of the sensor 102 was closer to the body of the user 104 than other times, such as when the user 104 was performing an inhalation breath movement that may affect the distance or orientation of the sensor 102 relative to the body of the user 104. Continuing the example, a lesser amplitude may represent a time when the detector or light source of the sensor 102 was farther from the body of the user 104, such as when the user 104 was performing an exhalation breath movement. Continuing the example, the period of time between a first time T1 and a second time T2 may represent a time period during which the user 104 was breathing normally, without performing a selected activity. The time period between the second time T2 and a third time T3 may represent a length of time during which the user 104 held their breath. The time period after the third time T3 may represent a length of time during which the user 104 was breathing while performing an activity, such as a fitness exercise.

The times at which the amplitude of the signal based on the first sensor data 114(1) deviates from a threshold amplitude value may be used to determine the times at which a breath movement occurred. The direction in which the amplitude deviates from the threshold amplitude value may be used to determine the type of breath movement. The amount by which the amplitude deviates from the threshold amplitude may be used to determine an amount or rate at which air was moved during the breath movement. The rate at which the deviations in amplitude occur and the rate at which the amplitude changes may be used to determine a breathing rate of the user 104. For example, FIG. 4 depicts portions of the first sensor data 114(1) that correspond to a first set of determined breath movements 118(1) after the first time T1 and before the second time T2, a second set of determined breath movements 118(2) after the second time T2 and before the third time T3, and a third set of determined breath movements 118(3) after the third time T3.

In the graph 400 shown in FIG. 4, second sensor data 114(2) may represent an example second signal determined using a strain gauge. For example, a strain gauge may include one or more electrical elements for which an electrical resistance changes as movement of the body of the user 104 causes the electrical elements to deflect. A signal represented by the second sensor data 114(2) may have an amplitude that indicates times when the electrical element(s) of the strain gauge were deflected by the body of the user 104. For example, FIG. 4 depicts the first set of determined breath movements 118(1) corresponding to peaks and troughs in the amplitude of the signal between the first time T1 and the second time T2, the second set of determined breath movements 118(2) corresponding to portions of the signal between the second time T2 and the third time T3, and the third set of determined breath movements 118(3) corresponding to portions of the signal after the third time T3.

In some implementations, a relationship between the signal represented by the first sensor data 114(1) and a signal represented by the second sensor data 114(2) may be used to improve precision when determining the times at which the determined breath movements 118 occurred, and characteristics of the determined breath movements 118. For example, a signal represented by the second sensor data 114(2), determined using a strain gauge, may have an inverse relationship to the signal represented by the first sensor data 114(1), determined using a PPG sensor.

Figure 5:
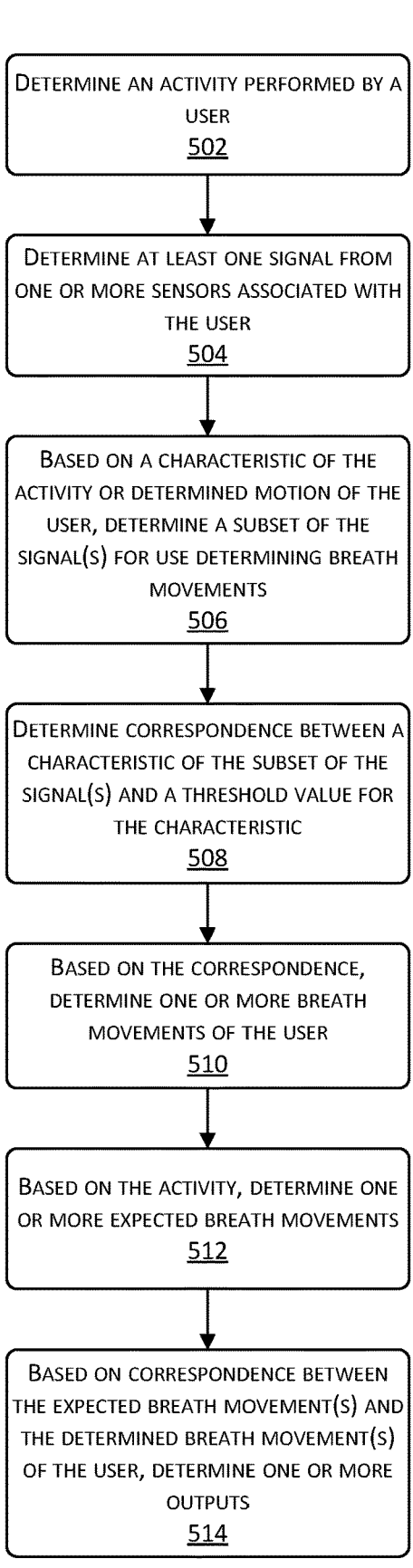
FIG. 5 is a diagram depicting an implementation of a process for determining breath movements of a user based on sensor data from one or more sensors.

FIG. 5 is a diagram 500 depicting an implementation of a process for determining breath movements of a user 104 based on sensor data 114 from one or more sensors 102. At 502, an activity performed by a user 104 may be determined. For example, a user 104 may select an activity from a list or other type of user interface, input a search query, and so forth. In some implementations, a user 104 may begin to preform an activity within a field of view of a camera 106, and the activity performed by the user 104 may be determined based on the motion, poses, or other characteristics of the activity, which may be determined based on video data 110 acquired using the camera 106. In some cases, one or more characteristics of the activity may be determined based on data acquired using other sensors 102, such as motion sensors, position sensors, physiological sensors, and so forth. Different activities may be associated with different characteristics. For example, an aerobic activity may be associated with significant motion of the user 104, rapid breathing, a rapid heart rate, and so forth. As another example, a generally static activity, such as meditation, may be associated with minimal motion of the user 104, steady breathing, a low heart rate, and so forth. As yet another example, a first fitness exercise, such as a weighted arm exercise, may be associated with minimal movement of the chest and abdomen, while a second exercise, such as a squatting exercise, may be associated with significant movement of the chest and abdomen.

At 504, at least one signal may be determined from one or more sensors 102 associated with the user 104. For example, as described with regard to FIGS. 1-4, a PPG sensor or other type of sensor 102 that emits light or another type of signal may be associated with a torso of the user 104, or a strain gauge may be associated with one or more fasteners secured to the torso of the user 104. In some implementations, a camera 106 may be used to determine a position of a chest or abdomen of the user 104. In other implementations, an accelerometer may be used to determine motion of one or more parts of the body of the user 104, which may include the chest or abdomen. In still other implementations, one or more microphones or sensors that detect the movement or presence of one or more gasses may be used to detect inhalation or exhalation of the user 104. Different sensors 102 may be suitable for use during activities having different characteristics. For example, a camera 106 or accelerometer may be suitable for determining movements of a chest or abdomen associated with breathing when an activity does not include significant movement of a user's torso, but may be unsuitable for such determinations if the activity includes such movement. However, in such cases, use of a PPG sensor or other type of sensor 102 secured to the torso of the user 104 in a manner that prevents relative movement between the sensor 102 and the body of the user 104 due to motion associated with performance of an activity may be suitable for acquisition of signals that may indicate breath movements of the user 104.

At 506, based on a characteristic of the activity, or on determined motion of the user 104, a subset of the signal(s) for use determining breath movements may be determined. For example, activity data 206, or another source of data, may indicate characteristics of an activity, or types of sensor data 114 that are suitable for determining breath movements during performance of the activity. In other implementations, an accelerometer, camera 106, or other type of sensor 102 may be used to determine motion of the user 104, and the activity data 206 or other source of data may associate types of sensors 102 or sensor data 114 that are suitable for use to determine breath movements when the determined motion is occurring. For example, if motion of the user 104 exceeds a threshold value, signals acquired using an accelerometer may be disregarded when determining breath movements, while signals acquired using a PPG sensor may be more heavily weighted than other signals.

At 508, correspondence between a characteristic of the subset of the signal(s) and a threshold value for the characteristic may be determined. For example, a characteristic of a signal may include an amplitude of the signal, and if the amplitude of the signal differs from a threshold amplitude by at least a threshold value, this difference may indicate a breath movement of the user 104. Other characteristics of the signal may include a frequency, strength, electrical resistance, and so forth. In some cases, correspondence between these characteristic(s) and one or more threshold values may be used to determine breath movements of the user 104.

For example, at 510, based on the correspondence between a characteristic of the signal(s) and a threshold value for the characteristic, one or more breath movements of the user 104 may be determined. Breath movements may include an inhalation breath movement, an exhalation breath movement, a rate or amount of air that is inhaled or exhaled, a breathing rate, and so forth. For example, an amplitude of a PPG signal that differs from a threshold amplitude in a first direction may indicate an inhalation breath movement, while an amplitude that differs from the threshold amplitude in a second direction opposite the first direction may indicate an exhalation breath movement. Rates of change of the amplitude may indicate a rate at which air is inhaled or exhaled, a breathing rate, and so forth. The amount by which an amplitude value differs from a threshold amplitude may indicate an amount of air inhaled or exhaled, or a rate at which the air is inhaled or exhaled.

At 512, based on the activity, one or more expected breath movements 120 may be determined. For example, activity data 206 may associate particular pose data 112 that represents a portion of an activity with a corresponding expected breath movement 120 to be performed when performing that portion of the activity. In some cases, the portion of an activity performed by the user 104 may be determined based on video data 110 acquired using one or more cameras 106. Based on the video data 110, pose data 112 that indicates one or more positions of the body of the user 104 may be determined. Correspondence between the determined pose data 112 and activity data 206 may be used to determine an expected breath movement 120 that corresponds to the pose of the user 104. In other cases, the expected breath movement 120 for a portion of the activity associated with instruction or other output that is presented may be determined.

At 514, based on correspondence between the expected breath movement(s) 120 and the determined breath movement(s) 118 of the user 104, one or more outputs may be determined. For example, an output may include an instruction, score, rating, or other type of feedback or information indicative of a difference between a determined breath movement 118 and expected breath movement 120, or confirmation of correspondence between the determined breath movement 118 and the expected breath movement 120.

FIG. 6 is a block diagram 600 depicting an implementation of a computing device 602 within the present disclosure. The computing device 602 may include one or more servers 116, user devices that incorporate cameras 106, output devices 108, or one or more other sensors 102, or other computing devices 602 in an environment with a user 104 or remote from the environment of the user 104. While FIG. 6 depicts a single block diagram 600 of a computing device 602, any number and any type of computing devices 602 may be used to perform the functions described herein. For example, data may be acquired and processed using one or more computing devices 602 in an environment with a user 104, while other data may be sent to one or more servers 116 for analysis or processing.

One or more power supplies 604 may be configured to provide electrical power suitable for operating the components of the computing device 602. In some implementations, the power supply 604 may include a rechargeable battery, fuel cell, photovoltaic cell, power conditioning circuitry, and so forth.

The computing device 602 may include one or more hardware processor(s) 606 (processors) configured to execute one or more stored instructions. The processor(s) 606 may include one or more cores. One or more clock(s) 608 may provide information indicative of date, time, ticks, and so forth. For example, the processor(s) 606 may use data from the clock 608 to generate a timestamp, trigger a preprogrammed action, and so forth.

The computing device 602 may include one or more communication interfaces 610, such as input/output (I/O) interfaces 612, network interfaces 614, and so forth. The communication interfaces 610 may enable the computing device 602, or components of the computing device 602, to communicate with other computing devices 602 or components of the other computing devices 602. The I/O interfaces 612 may include interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 612 may couple to one or more I/O devices 616. The I/O devices 616 may include any manner of input devices or output devices associated with the computing device 602. For example, I/O devices 616 may include touch sensors, displays, touch sensors integrated with displays (e.g., touchscreen displays), keyboards, mouse devices, microphones, image sensors, cameras, scanners, speakers or other types of audio output devices, haptic devices, printers, and so forth. I/O devices 616 may also include one or more types of sensors 102, such as PPG sensors, physiological sensors, accelerometers, motion sensors, position sensors, strain gauges, and so forth. In some implementations, the I/O devices 616 may be physically incorporated with the computing device 602. In other implementations, I/O devices 616 may be externally placed.

The network interfaces 614 may be configured to provide communications between the computing device 602 and other devices, such as the I/O devices 616, routers, access points, and so forth. The network interfaces 614 may include devices configured to couple to one or more networks including local area networks (LANs), wireless LANs (WLANs), wide area networks (WANs), wireless WANs, and so forth. For example, the network interfaces 614 may include devices compatible with Ethernet, Wi-Fi, Bluetooth, ZigBee, Z-Wave, 3G, 4G, 5G, LTE, and so forth.

The computing device 602 may include one or more buses or other internal communications hardware or software that allows for the transfer of data between the various modules and components of the computing device 602.

As shown in FIG. 6, the computing device 602 may include one or more memories 618. The memory 618 may include one or more computer-readable storage media (CRSM). The CRSM may be any one or more of an electronic storage medium, a magnetic storage medium, an optical storage medium, a quantum storage medium, a mechanical computer storage medium, and so forth. The memory 618 may provide storage of computer-readable instructions, data structures, program modules, and other data for the operation of the computing device 602. A few example modules are shown stored in the memory 618, although the same functionality may alternatively be implemented in hardware, firmware, or as a system on a chip (SoC).

The memory 618 may include one or more operating system (OS) modules 620. The OS module 620 may be configured to manage hardware resource devices such as the I/O interfaces 612, the network interfaces 614, the I/O devices 616, and to provide various services to applications or modules executing on the processors 606. The OS module 620 may implement a variant of the FreeBSD operating system as promulgated by the FreeBSD Project; UNIX or a UNIX-like operating system; a variation of the Linux operating system as promulgated by Linus Torvalds; the Windows operating system from Microsoft Corporation of Redmond, Washington, USA; or other operating systems.

One or more data stores 622 and one or more of the following modules may also be associated with the memory 618. The modules may be executed as foreground applications, background tasks, daemons, and so forth. The data store(s) 622 may use a flat file, database, linked list, tree, executable code, script, or other data structure to store information. In some implementations, the data store(s) 622 or a portion of the data store(s) 622 may be distributed across one or more other devices including other computing devices 602, network attached storage devices, and so forth.

A communication module 624 may be configured to establish communications with one or more other computing devices 602. Communications may be authenticated, encrypted, and so forth.

The memory 618 may also store the image analysis module 202. The image analysis module 202 may determine pose data 112 based on video data 110. For example, the image analysis module 202 may use one or more pose estimation algorithms to determine one or more poses of a user 104 based on one or more frames of video data 110. Continuing the example, the image analysis module 202 may include one or more object recognition or segmentation algorithms to identify portions of frames of video data 110 in which the user 104 is visible, portions of a frame of video data 110 that correspond to particular body parts of the user 104, and so forth.

The memory 618 may additionally store the activity module 204. The activity module 204 may determine an expected breath movement 120 based on correspondence between pose data 112 indicative of a position of a user 104

(which may correspond to a portion of an activity), and activity data 206 that associates an expected breath movement 120 with the portion of the activity represented by the pose data 112. For example, activity data 206 may associate one or more positions that are achieved during an activity, represented as pose data 112, with a corresponding expected breath movement 120. The activity module 204 may determine a portion of the activity, represented by pose data 112, that most closely corresponds to the pose data 112 determined using the image analysis module 202, and a particular expected breath movement 120 that is associated with the determined portion of the activity.

The memory 618 may store the signal analysis module 208. The signal analysis module 208 may determine one or more signal characteristics 210 based on sensor data 114. For example, a signal characteristic 210 may include an amplitude of a received signal, such as the strength or intensity of reflected light or another detectable signal detected by a sensor 102. Other signal characteristics 210 may include frequency, strength, rates of change of one or more signal characteristics 210, and so forth. In some implementations, the signal analysis module 208 may analyze signals from multiple sensors 102. For example, use of multiple sensors 102 may improve precision and reduce noise or uncertainty when determining breath movements of a user 104.

The memory 618 may also store the breath analysis module 212. The breath analysis module 212 may determine a breath movement based on signal characteristics 210 of one or more signals determined using a sensor 102. In some implementations, a breath movement may be determined based on breath data 214, which may associate signal characteristics 210 with breath movements. For example, breath data 214 may include one or more algorithms, rules, and so forth that correlate values for signal amplitude or other signal characteristics 210 with particular breath movements, such as inhalation and exhalation. Continuing the example, the breath data 214 may indicate deviations from a selected or average signal amplitude that correspond to an inhalation breath movement, an exhalation breath movement, other breath movements, and so forth. The breath data 214 may associate any combination of signal characteristics 210 from any number of signals, from one or more types of sensors 102, with corresponding breath movements.

The memory 618 may additionally store the output module 216. The output module 216 may determine output data 122 based on correspondence between a determined breath movement 118 and an expected breath movement 120. For example, output data 122 may indicate differences between a determined and expected breath movement, information, instruction, a score or rating, or another type of feedback, and so forth. In some implementations, the output data 122 may be determined based in part on presentation data 218, which may include one or more rules, algorithms, threshold values, and so forth that may be used to determine differences between a determined breath movement 118 and an expected breath movement 120, outputs that correspond to the differences, formats for presentation of the outputs, times for presentation of the outputs, and so forth.

Other modules 626 may also be present in the memory 618. For example, other modules 626 may include permission or authorization modules to enable a user 104 to provide authorization to acquire video data 110 of the user 104. For users 104 that do not opt-in or otherwise authorize acquisition of video data 110 that depicts the user 104, generation, transmission, or use of such video data 110 may be prevented. Other modules 626 may also include encryption modules to encrypt and decrypt communications between computing devices 602, authentication modules to authenticate communications sent or received by computing devices 602, a permission module to assign, determine, and manage user permissions to access or modify data associated with computing devices 602, user interface modules to generate interfaces for receiving input from users 104, and so forth.

Other data 628 within the data store(s) 622 may include configurations, settings, preferences, and default values associated with computing devices 602. Other data 628 may also include encryption keys and schema, access credentials, and so forth. Other data 628 may additionally include video or audio files for output, such as during performance of activities by a user 104.

In different implementations, different computing devices 602 may have different capabilities or capacities. For example, servers 116 may have greater processing capabilities or data storage capacity than user devices.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
a camera;
a photoplethysmograph (PPG) sensor comprising a light source and a detector;
one or more memories storing computer-executable instructions; and
one or more hardware processors to execute the computer-executable instructions to:
acquire video data using the camera, wherein the video data represents a user performing an activity;
determine a pose of the user based on the video data;
determine a portion of the activity that corresponds to the pose;
determine, based on activity data that associates expected breath movements with portions of the activity, an expected breath movement that corresponds to the portion of the activity;
determine a signal using the PPG sensor, wherein the signal represents light from the light source reflected by a torso of a body of the user;
determine, based on an amplitude of the signal, a breath movement of the user;
determine correspondence between the breath movement of the user and the expected breath movement that corresponds to the portion of the activity; and
present an instruction indicative of the correspondence between the breath movement of the user and the expected breath movement.

2. The system of claim 1, the one or more hardware processors to further execute the computer-executable instructions to:
determine a portion of the pose that indicates a position of the torso of the body of the user, wherein the breath movement is further determined based at least in part on the position of the torso of the body of the user.

3. The system of claim 1, the one or more hardware processors to further execute the computer-executable instructions to:
before the signal is determined using the PPG sensor, cause the light source to emit a first quantity of light;
determine a difference between a second quantity of light reflected by the torso of the body of the user and a threshold quantity of light;
cause the light source to emit a third quantity of light based on the difference; and
determine that a fourth quantity of light reflected by the torso of the body of the user is within a threshold value of the threshold quantity of light.

4. A method comprising:
acquiring video data using a camera, wherein the video data represents a user performing an activity;
determining, based on the video data, a portion of the activity being performed by the user;

determining, based on first activity data that associates expected breath movements with portions of the activity, an expected breath movement that corresponds to the portion of the activity being performed by the user;

determining a first signal using a first sensor, wherein the first signal is emitted from a first source secured relative to a body of the user and is at least partially reflected by a first portion of the body of the user;

determining, based on a first amplitude of the first signal, a first breath movement of the user during performance of the activity;

determining a first correspondence between the first breath movement of the user and the expected breath movement that corresponds to the portion of the activity being performed by the user; and presenting an output indicative of the first correspondence between the first breath movement of the user and the expected breath movement.

5. The method of claim 4, further comprising:

determining a pose of the user based on the video data, wherein the pose represents a position of the body of the user;

wherein the expected breath movement is determined based in part on the pose of the user.

6. The method of claim 4, further comprising:

determining a pose of the user based on the video data, wherein the pose represents a position of the body of the user;

wherein the portion of the activity being performed by the user corresponds to the pose.

7. The method of claim 4, further comprising:

determining one or more characteristics of the first signal that is at least partially reflected by the first portion of the body of the user; and determining one or more physiological values associated with the user based on the one or more characteristics of the first signal;

wherein the output is determined based in part on the one or more physiological values.

8. The method of claim 4, wherein the first signal represents first light from a first light source that is secured relative to the body of the user and is at least partially reflected by the first portion of the body of the user, the method further comprising:

before determining the first signal, causing the first light source to emit a first quantity of light;

determining a first value associated with at least a portion of the first quantity of light reflected by the body of the user;

determining a difference between the first value and a threshold value; and based on the difference, causing the first light source to emit a second quantity of light that differs from the first quantity of light, wherein the first signal is acquired based on the second quantity of light.

9. The method of claim 4, further comprising:

determining a second signal using a second sensor associated with the user;

determining a characteristic of the activity; and determining, based on second activity data that associates accuracy of signals with characteristics of activities, that the characteristic corresponds to the first signal;

wherein the first breath movement is determined based on the first signal in response to a second correspondence between the second activity data and the characteristic.

10. A system comprising:

a camera;

a first sensor;

one or more memories storing computer-executable instructions; and one or more hardware processors to execute the computer-executable instructions to:

acquire video data using the camera, wherein the video data represents a user performing an activity;

determine, based on the video data, a portion of the activity being performed by the user;

determine an expected breath movement that corresponds to the portion of the activity being performed by the user;

determine a first signal using the first sensor, wherein the first signal is one or more of emitted from or reflected by a first portion of a body of the user;

determine, based on a first characteristic of the first signal, a first breath movement of the user during performance of the activity;

determine a correspondence between the first breath movement of the user and the expected breath movement that corresponds to the portion of the activity being performed by the user; and present an output indicative of the correspondence between the first breath movement of the user and the expected breath movement.

11. The system of claim 10, wherein the first sensor comprises a photoplethysmograph (PPG) sensor that emits first light, and the one or more hardware processors to further execute the computer-executable instructions to:

determine one or more characteristics of the first light that is at least partially reflected by the body of the user; and determine one or more physiological values associated with the user based on the one or more characteristics.

12. The system of claim 10, wherein the first characteristic of the first signal includes an amplitude.

13. The system of claim 10, the one or more hardware processors to further execute the computer-executable instructions to:

based on the video data, determine a position of one or more of the first portion or a second portion of the body of the user;

wherein the expected breath movement is determined based on the position of the one or more of the first portion or the second portion of the body of the user determined using the video data.

14. The system of claim 10, the one or more hardware processors to further execute the computer-executable instructions to:

based on the video data, determine a position of the body of the user;

determine the portion of the activity that corresponds to one or more of the position of the body of the user or second output indicative of the activity; and determine the expected breath movement that corresponds to the portion of the activity being performed by the user.

* * * * *